US007336984B2

(12) United States Patent
Gough et al.

(10) Patent No.: US 7,336,984 B2
(45) Date of Patent: Feb. 26, 2008

(54) MEMBRANE AND ELECTRODE STRUCTURE FOR IMPLANTABLE SENSOR

(75) Inventors: David A. Gough, Cardiff, CA (US); Joseph Y. Lucisano, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 624 days.

(21) Appl. No.: 10/719,541

(22) Filed: Nov. 20, 2003

(65) Prior Publication Data
US 2004/0106857 A1   Jun. 3, 2004

Related U.S. Application Data

(63) Continuation of application No. 10/078,567, filed on Feb. 15, 2002, now Pat. No. 6,721,587.

(60) Provisional application No. 60/269,169, filed on Feb. 15, 2001.

(51) Int. Cl.
*A61B 5/05* (2006.01)
*A61B 5/00* (2006.01)
(52) U.S. Cl. .................. 600/345; 600/347; 600/365
(58) Field of Classification Search ............... 600/309, 600/345–366
See application file for complete search history.

(56) References Cited

U.S. PATENT DOCUMENTS

| 4,484,987 A | 11/1984 | Gough |
| 4,650,547 A * | 3/1987 | Gough ..................... 205/778 |
| 4,671,288 A | 6/1987 | Gough |
| 4,890,620 A | 1/1990 | Gough |
| 5,112,455 A * | 5/1992 | Cozzette et al. ........... 205/778 |
| 5,322,063 A | 6/1994 | Allen et al. |
| 5,660,163 A | 8/1997 | Schulman et al. |
| 5,882,494 A | 3/1999 | Van Antwerp |
| 5,964,993 A | 10/1999 | Blubaugh et al. |
| 2002/0156355 A1 | 10/2002 | Gough |

OTHER PUBLICATIONS

Armour, et al., "Application of chronic intravascular blood glucose sensor in dogs." *Diabetes*, 39:1519-1526, 1990.
Bremer, et al., "Benchmark data from the literature for evaluation of new glucose sensing technologies." *Diabetes Technol. Ther.*, 3:409-418 (2001).

(Continued)

*Primary Examiner*—Charles A. Marmor
*Assistant Examiner*—Navin Natnithithadha
(74) *Attorney, Agent, or Firm*—DLA Piper US LLP

(57) ABSTRACT

The invention is the design of a biological measuring device for the determination of the concentration of biomolecules (e.g. glucose) in an environment which is designed for implantation into an individual or for use in the context of an external apparatus. The device contains a composite membrane that is essentially entirely permeable to oxygen and permeable to larger biomolecules only in discrete hydrophilic regions. The membrane diffusionally limits the access of biomolecules to an enzyme, present in the hydrophilic region that catalyzes the oxidation of the biomolecule to produce hydrogen peroxide. A sensor in communication with the hydrophilic region is used to determine the amount of product produced or the amount of excess oxygen present allowing for the concentration of the biomolecule to be determined.

27 Claims, 6 Drawing Sheets

OTHER PUBLICATIONS

Choleau, et al., "Calibration of a subcutaneous amperometric glucose sensor Part 1. Effect of measurement uncertainties on the determination of sensor sensitivity and background current." *Biosens. Bioelectron.*, 17:647-654 (2002).

Choleau, et al., "Calibration of a subcutaneous amperometric glucose sensor implanted for 7 days in diabetic patients Part 2. Superiority of the one-point calibration method." *Biosens. Bioelectron.*, 17:641-646 (2002).

* cited by examiner

| | |
|---|---|
| MEMBRANE THICKNESS | 0.010" |
| ENZYME REGION SHAPE | FUNNEL |
| ENZYME REGION DIAMETER AT BASE | 0.028" |
| ENZYME REGION DIAMETER AT TOP | 0.006" |

| | |
|---|---|
| MEMBRANE THICKNESS | 0.010" |
| ENZYME REGION SHAPE | CYLINDRICAL |
| ENZYME REGION DIAMETER | 0.005" |
| ENZYME REGION SPACING | 0.010" CENTER-TO-CENTER OFFSET GRID PATTERN |

MEMBRANE AND ELECTRODE STRUCTURE FOR IMPLANTABLE SENSOR

CROSS-REFERENCES TO RELATED APPLICATIONS

This application claims the benefit of priority of U.S. provisional application Ser. No. 60/269,169 filed Feb. 15, 2001 which is incorporated herein by reference in its entirety.

STATEMENT OF GOVERNMENT INTEREST

The invention was made with Government support under Grant Number DK55064 awarded by the National Institutes of Health.

FIELD OF THE INVENTION

The invention relates to the design and use of a biological measuring device containing a novel membrane structure.

BACKGROUND OF THE INVENTION

It is standard practice to treat diabetes mellitus predominantly with insulin injections to compensate for the inability of the pancreas to make insulin to regulate blood glucose levels. The more tightly a person with diabetes is able to regulate his or her blood sugar, the less detrimental the disease is to overall health. The regulation of blood glucose would benefit from a glucose sensing device implanted in the body to monitor blood glucose levels at more frequent intervals than can be done with presently available repeated blood sampling.

A variety of biomedical measuring devices are routinely used by physicians and clinicians to monitor physiological variables such as respiratory rate, blood pressure and temperature. In addition to the repertoire of devices listed above is the enzyme electrode. Enzyme electrodes enable the user to determine the concentration of certain biochemicals rapidly and with considerable accuracy by catalyzing the reaction of a biochemical and a detectable coreactant or producing a product that may be readily sensed by well-known electrodes (e.g. oxygen, $H_2O_2$). Currently there are enzyme electrodes that can detect urea, uric acid, glucose, various alcohols, and a number of amino acids when used in certain well-defined situations.

A number of variations of the glucose enzyme electrode have been developed, all based on the same reaction catalyzed by glucose oxidase.

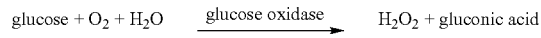

To accurately measure the amount of glucose present, both oxygen and water must be present in excess. As glucose and oxygen diffuse into an immobilized membrane phase, the glucose reacts with oxygen and water to produce $H_2O_2$ (hydrogen peroxide). Glucose is detected electrochemically using the immobilized enzyme glucose oxidase coupled to an oxygen- or hydrogen peroxide-sensitive electrode. The reaction results in a reduction in oxygen and the production of hydrogen peroxide proportional to the concentration of glucose in the sample medium.

The electrode can be polarized cathodically to detect residual oxygen not consumed by the enzymatic process, or polarized anodically to detect the product of the enzyme reaction, hydrogen peroxide. A functional device is composed of at least two detecting electrodes, or at least one detecting electrode and a reference signal source, to sense the concentration of oxygen or hydrogen peroxide in the presence and absence of enzyme reaction. Additionally, the complete device contains an electronic control means for determining the difference in the concentration of the substances of interest. From this difference, the concentration of glucose can be determined.

The enzyme catalase may be included in the oxygen-based system in excess in the immobilized-enzyme phase containing the glucose oxidase to catalyze the following reaction:

Hence, the overall reaction becomes:

This mixture of immobilized enzymes can be used in the oxygen-based device, but not the peroxide-based device. Catalase prevents the accumulation of hydrogen peroxide which can promote the generation of oxygen free radicals that are detrimental to health.

Glucose measuring devices for testing of glucose levels in vitro based on this reaction have been described previously (e.g. Hicks et al., U.S. Pat. No. 3,542,662) and work satisfactorily as neither oxygen nor water are severely limiting to the reaction when employed in vitro. Additionally, a number of patents have described implantable glucose measuring devices. However, certain such devices for implantation have been limited in their effectiveness due to the relative deficit of oxygen compared to glucose in tissues or the blood stream (1: 50-1000).

Previous devices (e.g. Fisher and Abel) have been designed such that the surface of the device is predominantly permeable to oxygen, but not glucose, and is in contact with the enzyme layer. Glucose reaches the enzyme layer through a minute hole in the oxygen-permeable outer layer that is in alignment with an electrode sensor beneath it. Hydrogen peroxide produced by the enzyme reaction must diffuse directly to the sensing anode or through a porous membrane adjacent to the electrode, but is otherwise substantially confined within the enzyme layer by the oxygen-permeable layer resulting in unavoidable peroxide-mediated enzyme inactivation and reduced sensor lifetime.

The strategy of designing devices with differentially permeable surface areas to limit the amount of glucose entering the device, while maximizing the availability of oxygen to the reaction site, is now common (Gough, U.S. Pat. No. 4,484,987). An example based on device geometry is seen in Gough, U.S. Pat. No. 4,671,288, which describes a cylindrical device permeable to glucose only at the end, and with both the curved surface and end permeable to oxygen. Such a device is placed in an artery or vein to measure blood glucose. In vascular applications, the advantage is direct access to blood glucose, leading to a relatively rapid response. The major disadvantage of vascular implantation is the possibility of eliciting blood clots or vascular wall damage. This device is not ideal for implantation in tissues.

An alternative geometrically restricted device assembly was described in Gough, U.S. Pat. No. 4,650,547. The patent teaches a "stratified" structure in which the electrode was first overlaid with an enzyme-containing layer, and second with a non-glucose-permeable membrane. The resulting device is permeable to oxygen over the entire surface of the membrane. However, glucose may only reach the enzyme through the "edge" of the device in a direction perpendicular to the electrode, thus regulating the ratio of the access of the two reactants to the enzyme.

Devices have been developed for implantation in tissue to overcome potential problems of safely inserting into, and operating sensors within, the circulatory system (e.g. Gough, U.S. Pat. No. 4,671,288); however, their accuracy may be limited by the lower availability of oxygen in tissues. The device membrane is a combination of glucose-permeable area and oxygen-permeable domains. The ratio of the oxygen-permeable areas to the glucose-permeable areas is somewhat limited due to the design.

To avoid geometric restrictions on devices, membranes that are variably permeable to oxygen and glucose have been developed (Allen, U.S. Pat. No. 5,322,063). Membrane compositions are taught in which the relative permeability of oxygen and glucose are manipulated by altering the water content of a polymeric formulation. The disadvantages of such a membrane may include sensitivity of the membrane performance to variables during manufacture and that regions of oxygen permeability may not be focused over electrodes within the device.

An alternative strategy to device construction is to incorporate an enzyme-containing membrane that is hydrophilic and also contains small hydrophobic domains to increase gas solubility, giving rise to differential permeability of the polar and gaseous reactants (e.g. Gough, U.S. Pat. Nos. 4,484,987 and 4,890,620). Such membranes readily allow for the diffusion of small apolar molecules, such as oxygen, while limiting the diffusion of larger polar molecules, such as glucose. The disadvantage is that the amount of hydrophobic polymer phase must be relatively large to allow for adequate oxygen permeability, thereby reducing the hydrophilic volume available for enzyme inclusion sufficient to counter inactivation during long-term operation.

Schulman et al. (U.S. Pat. No. 5,660,163) teach a device with a silicone rubber membrane containing at least one "pocket" filled with glucose oxidase in a gelatinous conductive solution located over a first working electrode. In a preferred embodiment, the length of the "pocket" is approximately 3 times its thickness to optimize the linearity between current and the glucose concentration measurement. Because the long axis of the "pocket" is oriented parallel to the electrode surface, this design may be less amenable to miniaturization for tissue implantation.

SUMMARY OF THE INVENTION

The invention is the design and use of a biological measuring device for implantation into an individual or for use in an external environment. The device contains an enzyme electrode to detect the coreactant or product (e.g. oxygen, $H_2O_2$, respectively) of an enzymatic reaction catalyzed by an oxidase (e.g. glucose oxidase, lactate oxidase, cholesterol oxidase) of the biological molecule of interest (e.g. glucose, lactate, cholesterol) with a limiting reagent or coreactant (e.g. oxygen). The device contains a differentially permeable membrane that limits the access of the biological molecule of interest, which is present in the device's environment at a relatively high concentration as compared to the coreactant, to the enzyme. (Expected ratios of biological molecule to coreactant concentrations (e.g. glucose concentration to oxygen concentration) in biological samples or environments may be expected to range up to 10:1 and beyond, expressed in units of mg/dl/mmHg.) Thus, the biological molecule becomes the limiting reagent in a critical zone within the enzyme-containing region of the membrane, allowing for its quantification by assaying the amount of product produced or the amount of unconsumed coreactant by means of an associated sensor or electrode, responsive to the coreactant or product.

The membrane is composed of a continuous or nearly continuous restricted-permeability membrane body, permeable to oxygen and essentially impermeable to larger biological molecules (e.g. glucose, lactate, cholesterol), and discrete hydrophilic regions, permeable to both biological molecules and oxygen (FIG. 1). The reactants diffuse from the environment into the device through a single surface of the device. The size, density, shape, and number of hydrophilic regions may be varied depending upon the bodily fluid, tissue, or environment into which the device is implanted or depending upon the choice of the associated sensor. As opposed to prior membranes which have restricted-permeability and hydrophilic surfaces at restricted locations on the device defined by device shape, or other sensors covered in membranes whose differential oxygen- and biological molecule-permeability is continuous, the location, number, shape, and size of the oxygen- and biological molecule-permeable regions may be modified to optimize the performance of the sensor.

The invention is a biological measuring device containing the composite membrane of the invention. The membrane of the invention can be optimized for detection of a number of biochemicals with a single or a plurality of detecting electrodes. Electrodes may be linked in any of a number of ways well known to those skilled in the art (e.g. Sargent and Gough, 1991, herein incorporated by reference). The size, shape, number, and location of the hydrophilic regions can be varied to deliver the appropriate ranges of the biological molecule and oxygen to the enzyme such that a detectable amount of product or consumed coreactant reaches the associated sensor.

The invention is a method to specify the optimal ratio of restricted-permeability membrane body to hydrophilic regions in the membrane, and to determine the optimal shape and arrangement of the hydrophilic regions in the membrane such that the concentrations of the reactants in the critical zone are limited by diffusion. Using the method of the invention, the sensor can be optimized for different reactions and enzymes for use in different tissues, bodily fluids or in an external sensor.

The invention is the use of the biological measuring device to monitor the level of a biological molecule, either by implantation in an individual or by use of the device in an external environment. In a preferred embodiment, the device is used to monitor glucose levels in an individual with diabetes.

BRIEF DESCRIPTION OF THE DRAWINGS

The present invention will be better understood from the following detailed description of an exemplary embodiment of the invention, taken in conjunction with the accompanying drawings in which like reference numerals refer to like parts.

DETAILED DESCRIPTION AND PREFERRED EMBODIMENTS

Definitions

Figure 2:
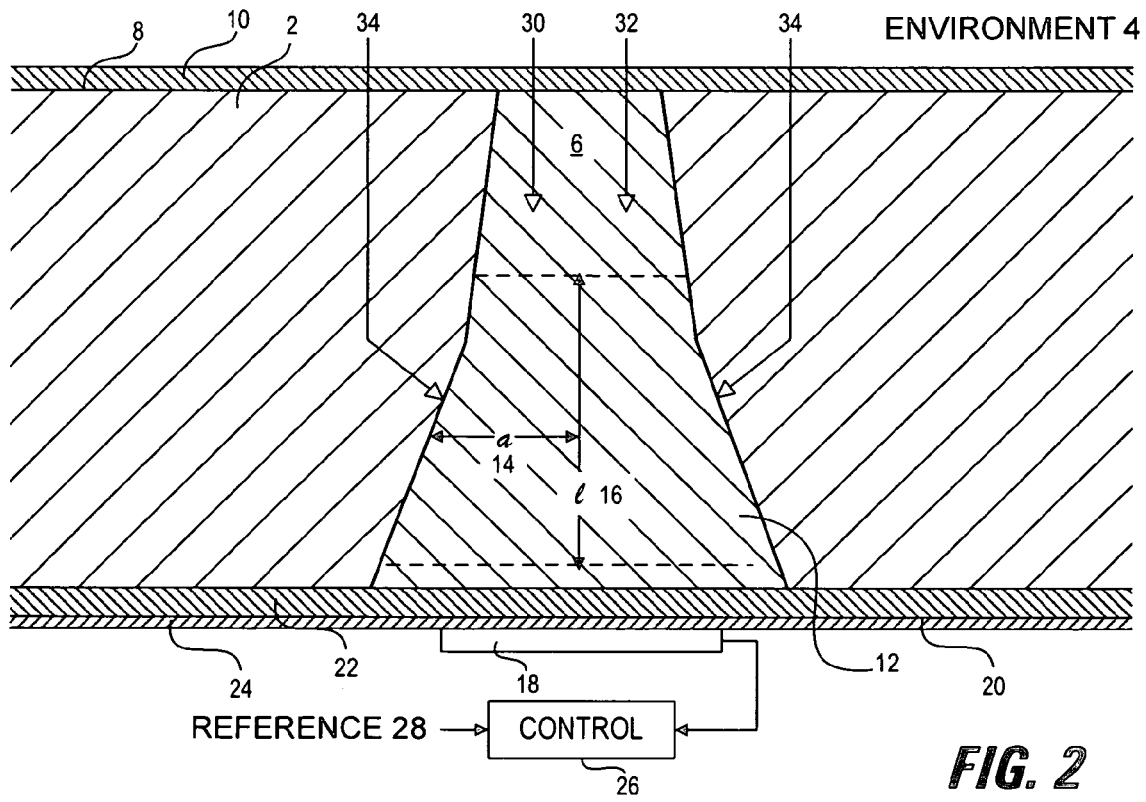
FIG. 2. Schematic of a biological sensor device for implantation. The sensor device for implantation comprises a membrane body (2) that communicates with an environment (4) having a first material such as glucose and a second material such as oxygen. The surface (8) of the membrane body communicates with the outer layer (10) to the environment (4). The membrane body communicates with a hydrophilic region (6) with catalyst. The hydrophilic region (6) contains a critical zone (12) of average equivalent radius a (14) and length/(16) such that a</. A sensor (18), with surface (20), is sensitive to the reaction product or residual co-reactant and produces a signal in proportion to the concentration. The sensor's surface (20) communicates with the electrolyte layer (24) adjacent to the sensor protective layer (22). A control (26) responds to the signal, for comparison with a reference (28). The diffusion paths of the first material (30) and (34) and of the second material (32) enter the device through the same surface (8).

Enzymatic sensor assembly—An electrochemical detector component, comprising a noble metal working electrode polarizable as an anode or a cathode, potential reference electrode, a counter electrode and layer of conductive electrolyte forming a thin conductive layer among the electrode sensor structures;

an electronic polarization and amplification component consisting of a potentiostat or polarizing amplifier, current recording amplifier and a signal conveyor (e.g. a wire); and a layered or stratified membrane structure composed (1) in the case of the oxygen based sensor of an inner, electrode protective layer of a pore-free, oxygen-permeable material such as polydimethylsiloxane that is impermeable to polar compounds, or in the case of a peroxide-based sensor, a porous membrane that is permeable to hydrogen peroxide and less permeable to larger polar molecules; (2) an enzyme region or domain of specified shape and volume containing immobilized enzymes; (3) a membrane structure for differential control of reactant access to the enzyme region by means of a specified pore size, differential permeability reactant solubility or geometric configuration; and (4) an optional biocompatibility membrane or layer to promote development of a biocompatible interface between tissue or blood and the implanted sensor (FIG. 2). A number of such assemblies are well known such as those taught in Schulman, U.S. Pat. No. 5,660,163.

Membrane body—A nearly continuous membrane that is permeable to oxygen and essentially non-permeable to larger biological molecules (e.g. glucose). It may or may not be water-containing and can be made of any of a number of oxygen-permeable polymeric materials including, but not limited to, any of the family of silicone-containing, ethylene-containing and propylene-containing polymers, with and without fluorine, such as silicone rubbers, polyethylene, polypropylene, Teflons, polyfluorinated hydrocarbons or similar polymers, as well as certain hydrophilic polymers, such as polyhydroxyethlymethacrylate of limited molecular porosity, that are permeable to oxygen by virtue of having significant oxygen solubility or diffusivity. Co-polymers, blends, or composites that incorporate these types of materials are also suitable.

Hydrophilic region—An intermittent volume in communication with the membrane body that is permeable to both larger biological molecules (e.g. glucose) and oxygen. It can be made of any of a number of glucose- and oxygen-permeable materials including, but not limited to, polyacrylamide gels, glutaraldehyde cross-linked proteins, particularly collagen or albumin, vinyl pyrollidone, alginates, ethylene oxide, polyhydroxyethylmethacrylate and its derivatives, and other hydrophilic polymers and co-polymers. Co-polymers, blends, or composites that incorporate these types of materials are also suitable. An enzyme or catalyst is typically incorporated into this region.

Critical zone—A volume of the membrane that is coincident with the hydrophilic region, or a portion thereof, through which the reaction of the biological molecule with the oxygen is modulated by limiting the diffusion of the biological molecule from the environment. Preferably, it is a volume that is coincident with a given hydrophilic region, or a portion thereof that is bound between two end planes that are oriented perpendicular to the average vector direction of diffusion of the biological molecule (e.g. glucose) throughout the whole given hydrophilic region, wherein the average vector direction of diffusion of the biological molecule in the critical zone is essentially parallel to the average vector direction of diffusion of the biological molecule in the whole given hydrophilic region. Additionally, a critical zone must have an average equivalent radius that is less than the length of the critical zone. An equivalent radius is obtained by first dividing by pi the area of a given cross section of a given hydrophilic region, the area being oriented perpendicular to the average vector direction of diffusion of the biological molecule throughout the whole given hydrophilic region, then taking the square root of the resulting quantity.

Detailed Description

The invention is a novel membrane structure based on a nearly continuous oxygen-permeable, glucose-impermeable membrane body having discrete regions of hydrophilic, glucose-permeable gel in which the enzyme is immobilized. Additionally, the hydrophilic regions communicate through the membrane to one or more underlying electrode sensor structures. The materials and methods used for preparing the hydrophilic regions are described in Gough, U.S. Pat. No. 4,484,987 which is incorporated herein by reference.

The desired geometric relationships between the membrane body and the hydrophilic regions and the shape of the hydrophilic regions must function to supply coreactant to the enzyme gel such that the reaction within the gel is limited by the availability of biological molecule rather than coreactant. Any portion of the hydrophilic region that meets the definition of critical zone may provide this function. The hydrophilic regions may or may not penetrate the entire thickness of the membrane, but must communicate, either directly or by means of an external membrane having permeability to glucose, with the environment in which the device is operated. In a preferred embodiment, the device is a flat, disc shape. The glucose and oxygen diffuse into the device through a single face at the device-environment interface.

The hydrophilic regions may be varied in size, shape, number and spatial distribution to advantage in a given device design. Shapes may include: 1) a cylinder orthogonal to the plane of the membrane to provide radially uniform oxygen access within the enzyme region, 2) a square or parallelogram, as seen from the face of the membrane, for ease of fabrication by a method of laying one sheet of hydrophobic strips over another, 3) a cone or other shape of tapering radius, as seen from the edge of the membrane with the base at the sensor electrode side to provide a mechanical confinement of the gel and prevent gel extrusion or separation from the membrane body during fabrication or use conformations formed from a combination of such shapes, such as a "funnel," formed by the combination of conically- and cylindrically-shaped regions (e.g. FIGS. 2-3). The exact conformation of the shapes listed above is not required.

Figure 4:
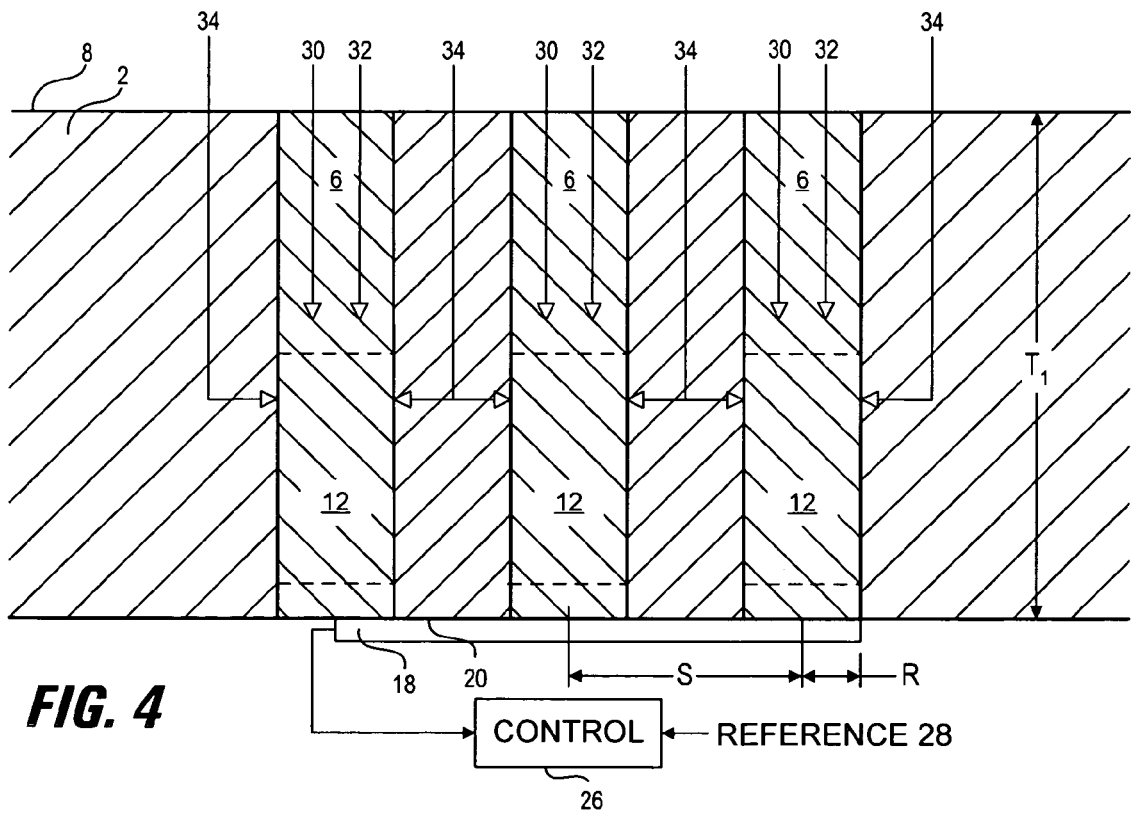
FIG. 4. Schematic of membrane illustrating a plurality of hydrophilic regions. This figure describes a sensor device with a membrane body (2) with a plurality of hydrophilic regions (6) with catalyst variously juxtaposed across the sensor surface (20) in communication with the sensor (18), the hydrophilic regions having respective critical zones (12). The diffusion paths for the first material (30) and (34), and second material (32) enter the device through the same surface (8). The sensor (18) with the surface (20) is sensitive to the reaction product or residual co-reactant and produces a signal in proportion to the concentration. The center-to-center spacing (S) and the radius (R) of the hydrophilic regions is shown.

The size, shape, number, and spatial distribution of the hydrophilic gel regions can be varied (e.g. FIG. 4). The exact patterning of the hydrophilic gel regions is designed to optimize sensor response, sensitivity to biologic molecule, coreactant independence and insensitivity to environmental heterogeneity. The size of the hydrophilic regions can be varied over different electrodes to provide the sensor with a broader range of sensitivity. It is not necessary for the sensor to be of the same radius as the hydrophilic region. Moreover, it is possible to design a device with multiple sensors associated with a single hydrophilic region, or multiple hydrophilic regions associated with a single sensor. Design choices are based on a variety of factors, such as preference for a particular manufacturing technique, requirements for signal magnitudes based on choice of electronic circuitry, and the vascular density in the tissue of implantation.

The thickness of the membrane can be controlled to optimize the oxygen independence, diffusional length for glucose within the hydrophilic gel to provide reserve enzyme, and to optimize respective response times to glucose and oxygen changes.

Regions of the membrane body that can be used to house hydrophilic regions may be fabricated by any of a number of methods well known to those skilled in the art including programmed laser ablation, molding, cutting, punching, etc. Holes can then be filled with uncrosslinked enzyme-containing precursor solutions and then crosslinker is added or activated, to solidify the solution.

A hydrophobic membrane, shown in FIG. 2, may be inserted between the above-described membrane structure and the oxygen sensing electrode, or directly overlying the oxygen electrode and electrolyte solution. Such an intervening membrane protects the oxygen electrode from electrochemical poisoning from polar and diffusable compounds. Its dimensions and material properties can also be varied to advantage depending on the exact sensor design. Preferably such a membrane would readily allow the diffusion of oxygen while preventing the diffusion of larger molecules through the membrane. Additionally, the membrane is thin to maximize the sensitivity of the system to glucose.

The positioning and arrangement of the hydrophilic gel regions can be varied with regard to the underlying oxygen sensor electrode or electrodes to optimize the sensitivity and range of the device. It is important to note that the sensitivity and response time of the device can be altered simply by varying the amount of electrode surface area of the oxygen sensor, along with the thickness of the membrane over the sensor. The methods for making these adjustments are well known to those skilled in the art.

A number of electrodes and electrode combinations are well known to those skilled in the art and could be used in this invention. For example, the electrodes may be either oxygen or hydrogen peroxide sensing. The sensor may be an electrically conductive layer or an electrode connected by a wire to single or multichannel electronics. Alternatively, the membrane may be connected directly to the electronics.

In embodiments of the invention for implantation into the body, the sensor may be covered with a biocompatible outer membrane that also inhibits exposure of the inner membranes to proteins or other large molecules that may alter the properties of the sensor inner membranes. Such a membrane could be composed of porous polyhydroxyethyl-methacrylate, polyethylene- or polycarbonate-containing polymers, fluorinated polymers, or other suitable materials.

Desirable sizes and shapes of hydrophilic regions and associated membranes can be calculated by a systematic, computational approach. In a preferred embodiment, the device contains at least one hydrophilic region over a single electrode (FIGS. 1-4). The sensor is a disc platinum oxygen electrode closely apposed to a hydrophilic region and the hydrophilic region is surrounded by a material that is essentially impermeable to glucose. The hydrophilic region contains immobilized glucose oxidase and optionally, an excess of catalase. For a given glucose concentration in the external medium the sensor response is determined by the permeability of the hydrophilic region and membrane body, the enzyme activity, and the aspect ratio, or ratio of the average equivalent radius of the critical zone within the hydrophilic region to the height of the critical zone. In order to obtain a useful range of response in biological operating conditions, it is preferred that this aspect ratio be less than one.

EXAMPLE 1

Sensor membranes were produced by filling the cavities in perforated silicone rubber sheets with a glucose oxidase/albumin mixture and crosslinking the mixture with glutaraldehyde using the method described in Armour et al. 1990, incorporated herein by reference.

The membranes were mounted over a membrane-covered electrochemical oxygen sensor, with a circular platinum working electrode of diameter 0.005", formed on an alumina ceramic substrate using conventional thick-film methods. The required counter electrode was platinum and the required reference electrode was silver-plated platinum.

The devices were connected to a potentiostat circuit, and the working electrode was polarized at −500 mV with respect to the reference electrode. (see for example: Bard and Faulkner, 2000).

Figure 5:
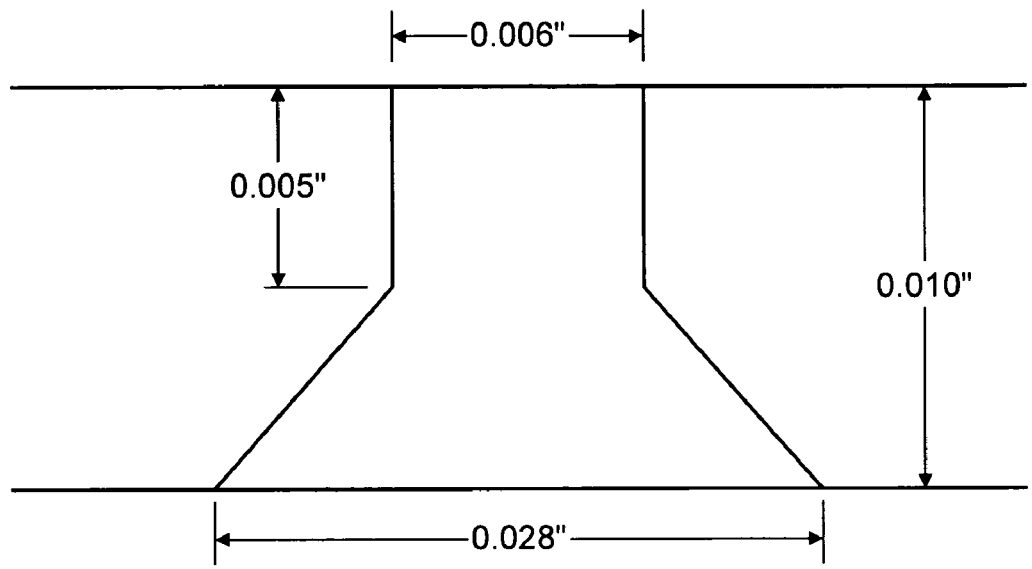
FIG. 5. Schematic of a membrane illustrating a funnel shaped hydrophilic region as discussed in Example 1 with various specification measurements indicated, including membrane thickness, enzyme region diameter at environment, enzyme region diameter at sensor and height of cylindrical portion of funnel.

Tests were conducted in a simulated biological environment: phosphate-buffered saline, at 37° C., equilibrated with known oxygen concentrations. Known quantities of glucose were added to the solution and the electrode current measured. Two different membrane geometries, schematically represented in FIG. 5, with the specifications shown below, were tested. As is well-known (see e.g. Gough et al, 1985), the device's response is suitably analyzed by examination of the normalized electrode current as a function of the glucose-to-oxygen ratio in the environment. Both raw (nanoampere) electrode currents and normalized currents (expressed as a percentage of the value without glucose) are reported below.

Specifications:

| membrane thickness: | 0.010" |
| hydrophilic region shape: | funnel |
| hydrophilic region radius at base (closest to electrode): | 0.014" |
| hydrophilic region raduis at top, communicating with fluid: | 0.003" |

Results:

| [glucose]/[oxygen] (mg/dl/mmHg) | electrode current (nanoamperes) | electrode current (% of initial) |
| --- | --- | --- |
| 0 | 12.8 | 100 |
| 0.98 | 10.6 | 83 |
| 2.7 | 9.3 | 73 |
| 5.9 | 7.5 | 59 |
| 10.8 | 5.7 | 45 |
| 22.1 | 1.0 | 8 |

Specifications:

| membrane thickness: | 0.010" |
| hydrophilic region shape: | funnel |
| hydrophilic region radius at base (closest to electrode): | 0.014" |
| hydrophilic region radius at top, communicating with fluid: | 0.002" |

Results:

| [glucose]/[oxygen] (mg/dl/mmHg) | electrode current (nanoamperes) | electrode current (% of initial) |
| --- | --- | --- |
| 0 | 9.9 | 100 |
| 1.2 | 8.9 | 90 |
| 2.8 | 8.3 | 84 |
| 5.7 | 7.4 | 75 |
| 11.1 | 6.3 | 64 |
| 22.7 | 3.5 | 35 |
| 42.8 | 1.2 | 12 |

EXAMPLE 2

Sensor membranes were produced by filling the cavities in perforated silicone rubber sheets with a glucose oxidase/albumin mixture and crosslinking the mixture with glutaraldehyde using the method described in Armour et al. 1990, incorporated herein by reference. The membranes were mounted over a membrane-covered electrochemical oxygen sensor, with a rectangular platinum working electrode of dimensions 0.025" (inches)×0.2", formed on an alumina ceramic substrate using conventional thick-film methods. The required counter electrode was platinum and the required reference electrode was silver-plated platinum.

The devices were connected to a potentiostat circuit, and the working electrode was polarized at −500 mV with respect to the reference electrode, following well-known methods (see for example: Bard and Faulkner, 2000).

Figure 6:
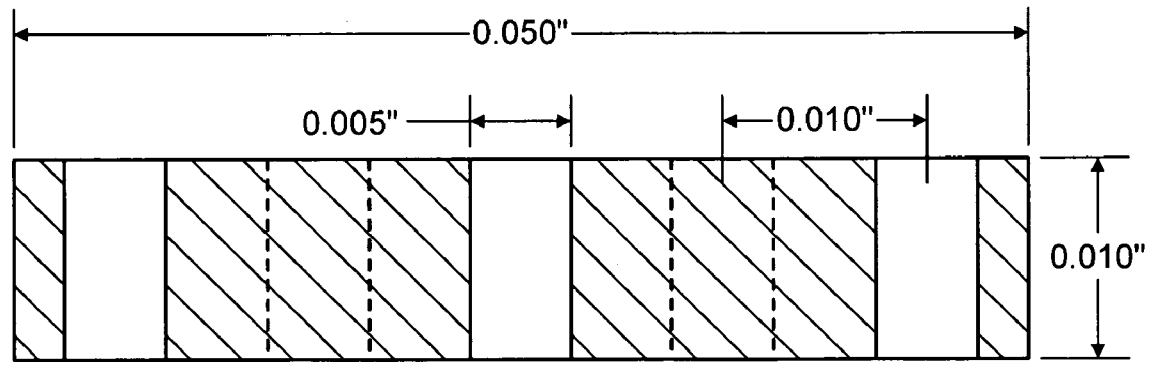
FIG. 6. Schematic of a membrane illustrating multiple cylindrical hydrophilic regions as discussed in Example 2 with various specification measurements indicated, including membrane thickness, enzyme region diameter and enzyme region spacing.
Figure 7A:
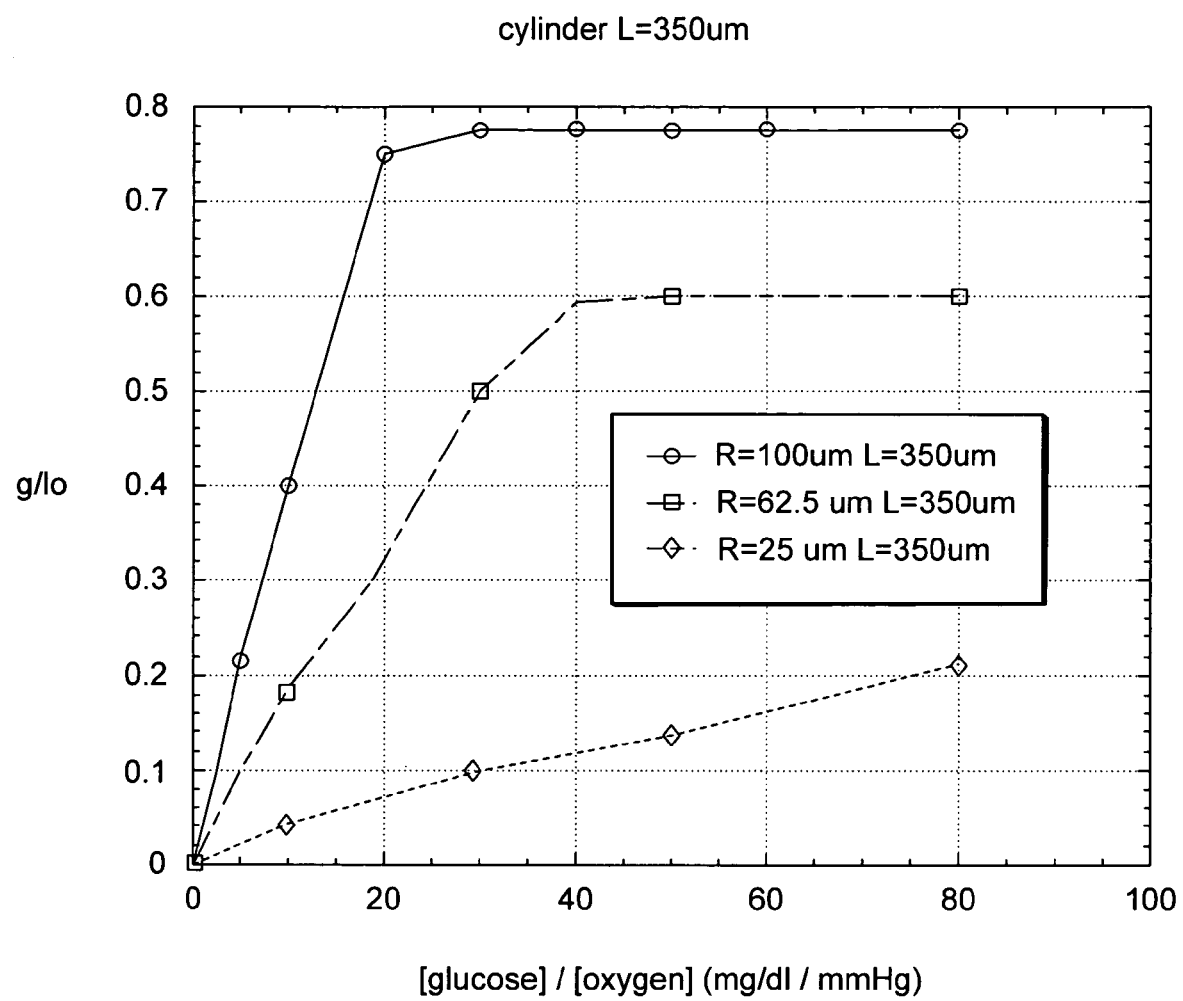
FIG. 7. The calculated response of an oxygen sensor, in communication with hydrophilic regions, to environmental concentrations of glucose and oxygen for various membrane constructions. The electrode current is calculated and shown as $i_g/l_o$ which is the ratio of the glucose modulated oxygen current to the current in the absence of glucose.
Figure 7B:
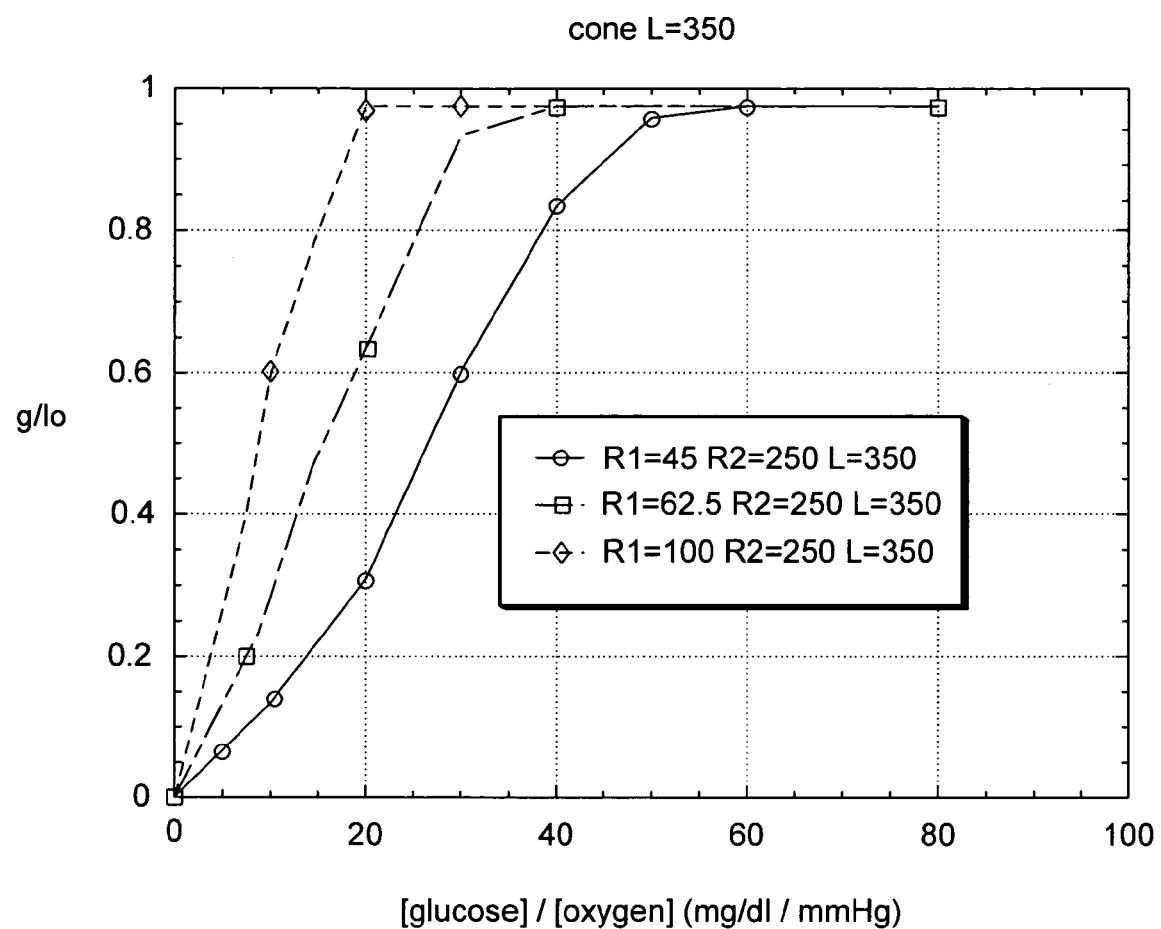
Figure 7C:
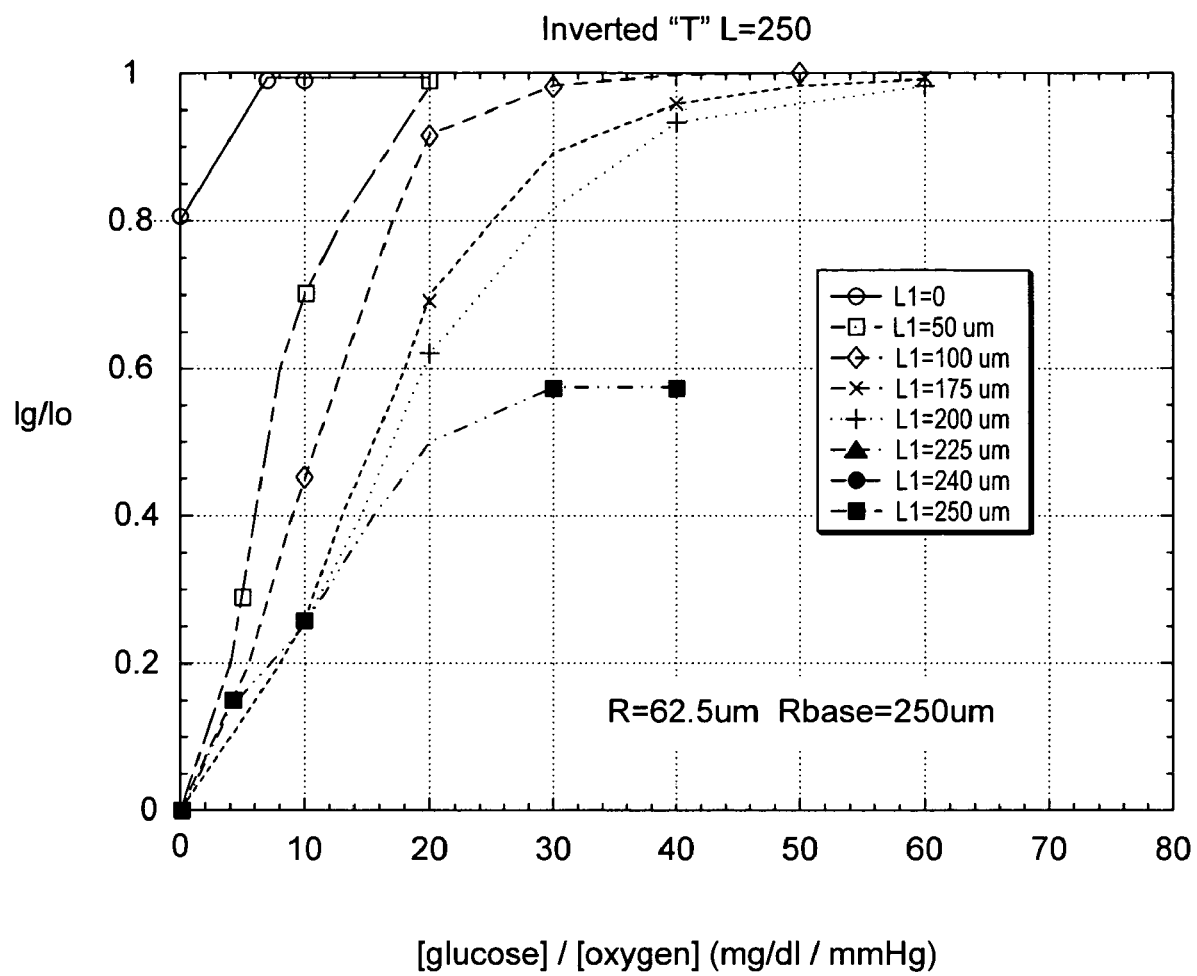

Tests were conducted in a simulated biological environment: phosphate-buffered saline, at 37° C., equilibrated with known oxygen concentrations. Known quantities of glucose were added to the solution and the electrode current measured. Two different membrane geometries, schematically represented in FIG. 6, with the specifications shown below, were tested. As is well-known (see e.g. Gough et al., 1985), the device's response is suitably analyzed by examination of the normalized electrode current as a function of the glucose-to-oxygen ratio in the environment. Both raw (nanoampere) electrode currents and normalized currents (expressed as a percentage of the value without glucose) are reported below.

Specifications:

| | |
|---|---|
| membrane thickness: | 0.010" |
| hydrophilic region shape: | cylindrical |
| hydrophilic region radius: | 0.005" |
| hydrophilic region spacing: | 0.020" center-to-center, offset grid pattern |

Results:

| [glucose]/[oxygen] (mg/dl/mmHg) | electrode current (nanoamperes) | electrode current (% of initial) |
|---|---|---|
| 0 | 74 | 100 |
| 0.6 | 54 | 73 |
| 1.1 | 45 | 61 |
| 2.2 | 36 | 49 |
| 2.8 | 31 | 42 |
| 4.2 | 26 | 35 |
| 5.6 | 22 | 30 |
| 11.2 | 14 | 19 |
| 22.4 | 8 | 11 |
| 44.9 | 5 | 7 |

Specifications:

| | |
|---|---|
| membrane thickness: | 0.010" |
| hydrophilic region shape: | cylindrical |
| hydrophilic region radius: | 0.005" |
| hydrophilic region spacing: | 0.010" center-to-center, offset grid pattern |

Results:

| [glucose]/[oxygen] (mg/dl/mmHg) | electrode current (nanoamperes) | electrode current (% of initial) |
|---|---|---|
| 0 | 192 | 100 |
| 0.6 | 123 | 64 |
| 1.1 | 89 | 46 |
| 2.2 | 53 | 28 |
| 2.8 | 45 | 23 |
| 4.2 | 31 | 16 |
| 5.6 | 35 | 13 |
| 11.2 | 6 | 3 |
| 22.4 | 2 | 1 |

EXAMPLE 3

Optimization of hydrophilic region shape and size was carried out using computer modeling methods. The analysis is based on the modeling of diffusion and reaction of glucose and oxygen in the presence of glucose oxidase and catalase within the hydrophilic region. The chemical reaction can be summarized as follows:

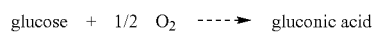

$$\text{glucose} + 1/2\ O_2 \dashrightarrow \text{gluconic acid}$$

Computer models of operating devices were constructed using conventional methods (see for example: Jablecki and Gough, 2000, incorporated herein by reference) to calculate the response of an oxygen sensor, in communication with one or more hydrophilic regions, to environmental glucose and oxygen concentrations for various membrane constructions. In these analyses, the electrode current is calculated and shown as $i_g/I_o$, which is the ratio of the glucose-modulated oxygen current to the current in the absence of glucose (see e.g. Armour, et al 1990). This normalized current equals zero in the absence of glucose and rises to a maximum value of unity as glucose concentration increases.

In all cases, useful sensitivities for monitoring glucose in biological media are obtainable only if the average equivalent radius of the hydrophilic region's critical zone is less than the length of the critical zone. If the average equivalent radius is greater than the length, then the critical zone is not adequately supplied with coreactant and the device's dynamic response range is too limited for practical use in biological samples.

Figure 1:
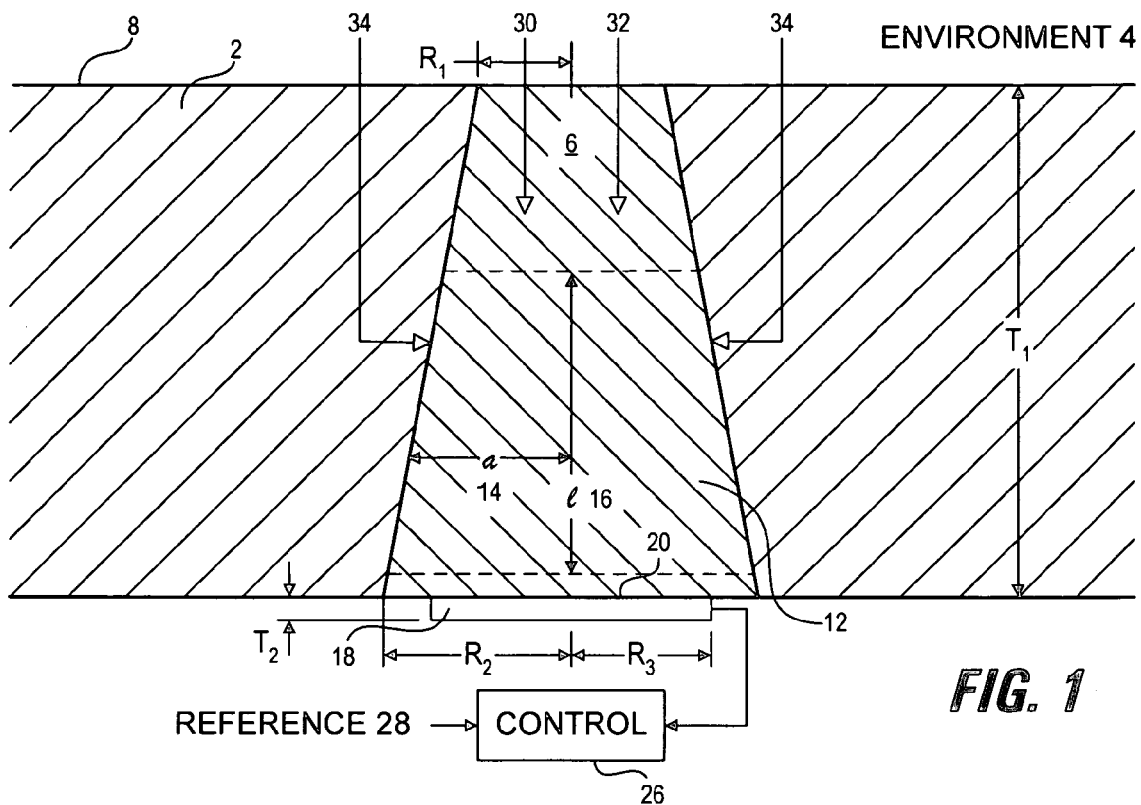
FIG. 1. Schematic of a biological sensor device membrane with a single hydrophilic region and sensor. The device comprises a membrane body (2) that communicates with an environment (4) having a first material such as glucose and a second material such as oxygen. The surface (8) of the membrane body communicates with the environment (4). The membrane body communicates with a hydrophilic region (6) with catalyst. The hydrophilic region (6) contains a critical zone (12) of average equivalent radius a (14) and length/(16) such that a</. A sensor (18), with surface (20), is sensitive to the reaction product or residual co-reactant and produces a signal in proportion to the concentration. A control (26) responds to the signal, for comparison with a reference (28). The diffusion paths of the first material (30) and (34) and of the second material (32) enter the device through the same surface (8). $R_1$ is the radius of the hydrophilic region on the face of the membrane in communication with the environment. $R_2$ is the radius of the hydrophilic region on the face of the membrane in communication with the sensor. $R_3$ is the radius of the sensor.
Figure 3:
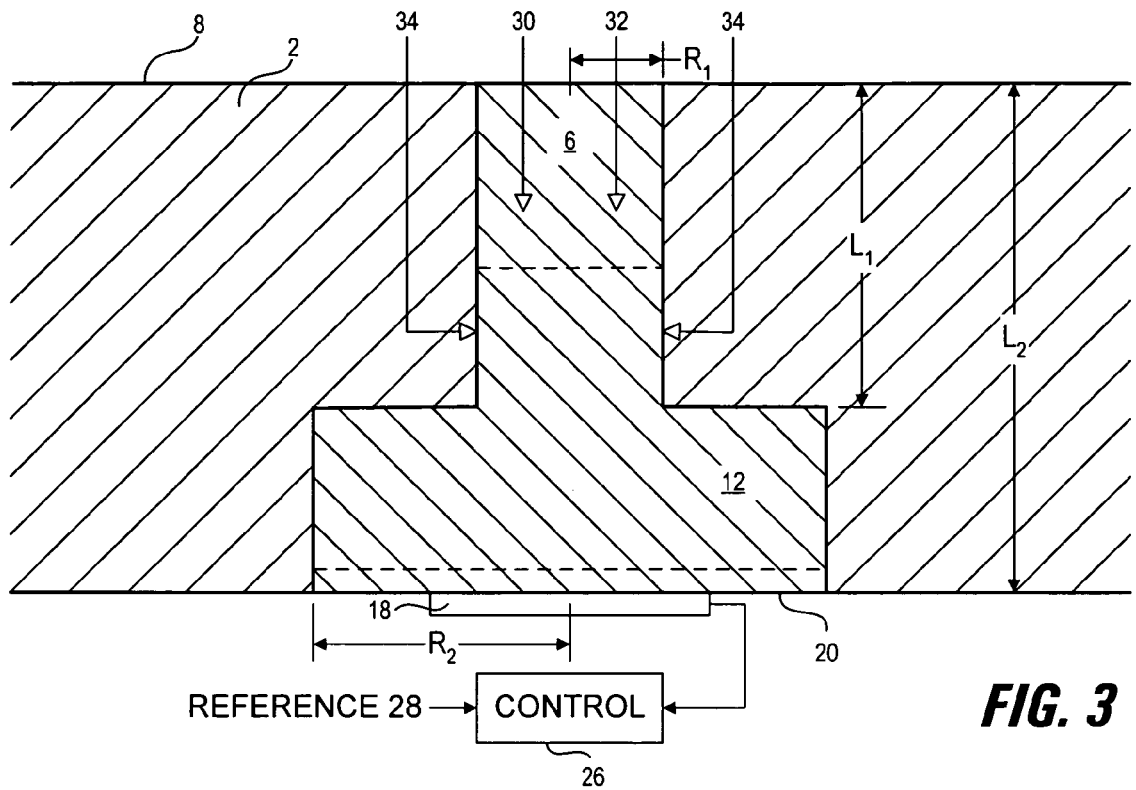
FIG. 3. Schematic of a biological sensor device with an alternative hydrophilic region. A biological sensor device having a hydrophilic region with catalyst with a cross-section in the form of an inverted "T". The device comprises a membrane body (2) that communicates with an environment having a first material such as glucose and a second material such as oxygen. The surface (8) of the membrane body communicates with the environment. The membrane body communicates with a hydrophilic region (6) with catalyst. The hydrophilic region (6) contains a critical zone (12) of average equivalent radius a and length/such that a</. A sensor (18), with surface (20), is sensitive to the reaction product or residual co-reactant and produces a signal in proportion to the concentration. A control (26) responds to the signal, for comparison with a reference (28). The diffusion paths of the first material (30) and (34) and of the second material (32) enter the device through the same surface (8). L1 is the length of the narrower cylindrical portion of the hydrophilic region and L2 is the full length of the hydrophilic region. In this representation, L2 is equivalent to T1 as shown in FIGS. 1 and 4.

The response range and sensitivities were modeled for three different shapes of hydrophilic regions analogous to those shown in FIGS. 4, 1 and 3, respectively. The data demonstrate that parameters may be readily modified by altering the shape of the hydrophilic region depending on other device considerations well known to those skilled in the art.

FIG. 6A shows the calculated response of an oxygen sensor (radius 62.5 microns) in communication with a membrane containing a cylindrical hydrophilic region, of length 350 microns, for various cylinder radii R. In all cases, the cylinder radius is less than the length, and the modeled devices demonstrate acceptable response to glucose.

FIG. 6B shows the calculated response of an oxygen sensor (radius 62.5 microns) in communication with a membrane containing a conical hydrophilic region, with a base radius R2 equal to 250 microns, and various values of top radii R1. The cone base is oriented toward the oxygen sensor and the length is 350 microns. In all cases, the average equivalent radius of the hydrophilic region is less than the length, and the modeled devices demonstrate acceptable response to glucose.

FIG. 6C shows the calculated response of an oxygen sensor (radius 62.5 microns) in communication with a membrane containing the inverted "T"-shaped cross-section hydrophilic region that is depicted schematically in FIG. 3, with a hydrophilic region base radius equal to 250 microns, and a top radius R equal to 62.5 microns. The total length of the "T" is 250 microns and the responses of the sensor for various lengths L1 of the small radius section are shown for L1=0 to L1=250 microns. Note that for critical zone aspect ratios of radius-to-length greater than 1, the dynamic range of the device is too limited for use in many biological or physiological media. In all cases when the average equivalent radius of the hydrophilic region critical zone is less than the length, the modeled devices demonstrate an acceptable range of response to glucose.

In the optimization calculation, circular cross-sections are used to determine the preferred size of the hydrophilic regions. However, this does not limit the instant invention to the use of round hydrophilic regions. The optimization calculation provides ideal internal and external surface areas and spacing for the hydrophilic regions that may be any shape. The selection of shape is a matter of choice to be made based on any of a number of factors including the shape of the electrodes, the overall shape of the sensor and the ease of manufacture.

Although an exemplary embodiment of the invention has been described above by way of example only, it will be understood by those skilled in the field that modifications may be made to the disclosed embodiment without departing from the scope of the invention, which is defined by the appended claims.

REFERENCES

Armour, J. C., J. Y. Lucisano, B. D. McKean and D. D. Gough "Application of a Chronic Intravascular Blood Glucose Sensor in Dogs," Diabetes 39:1519-26 (1990).

Bard, A. J. and Faulkner, L. R., *Electrochemical Methods: Fundamentals and Applications*, 2nd edition (December 2000), John Wiley & Sons.

M. C. Jablecki and D. A. Gough, "Simulations of the Frequency Response of Implantable Glucose Sensors." Analytical Chemistry 72(8), 1853-1859 (2000).

Gough, D. A., J. Y. Lucisano and P. H. S. Tse, "A Two-Dimensional Enzyme Electrode Sensor for Glucose," Anal. Chem. 57 (1985), 2351-7.

Sargent, B. J. and D. A. Gough, "Design and Validation of the Transparent Oxygen Sensor Array," IEEE Trans. Biomed. Engin. 38 (1991), 476-82.

The invention claimed is:

1. A measuring device for determining concentration of a first material in an environment in contact with the device, which first material reacts within said device in presence of a catalyst with a second material to form a third material; and which device comprises:

a membrane comprising a body, a surface in contact with said environment, and at least one discrete hydrophilic region in communication with said body, wherein said hydrophilic region is permeable to said first and second materials, and said body is otherwise permeable to said second material and essentially impermeable to said first material, wherein both said first and second materials diffuse into said device from said environment through said surface;

a catalyst within said hydrophilic region wherein reaction of said first and second materials occurs; at least one critical zone within said hydrophilic region containing said catalyst;

at least one sensor, having a surface communicating with at least one said hydrophilic region and sensitive to either said second material or said third material and producing a signal indicative of the concentration of said second or third material in said region; and a control responsive to said signal for comparing said signal to a reference to determine the concentration of said first material in said environment;

wherein further an average vector direction of diffusion of said first material in said critical zone is substantially parallel to an average vector direction of diffusion of said first material in said hydrophilic region.

2. A measuring device for determining concentration of a first material in an environment in contact with the device, which first material reacts within said device in presence of a catalyst with a second material to form a third material; and which device comprises:

a membrane comprising a body, a surface in contact with said environment, and at least one discrete hydrophilic region in communication with said body, wherein said hydrophilic region is permeable to said first and second materials, and said body is otherwise permeable to said second material and essentially impermeable to said first material, wherein both said first and second materials diffuse into said device from said environment through said surface;

a catalyst within said hydrophilic region wherein reaction of said first and second materials occurs; at least one critical zone within said hydrophilic region containing said catalyst, wherein the critical zone has a length and an average equivalent radius less than said length of said critical zone, wherein further said equivalent radius is obtained by dividing the cross-sectional area of said critical zone by pi and then taking a square root of the resulting quantity;

at least one sensor, having a surface communicating with at least one said hydrophilic region and sensitive to either said second material or said third material and producing a signal indicative of the concentration of said second or third material in said region; and a control responsive to said signal for comparing said signal to a reference to determine the concentration of said first material in said environment.

3. A measuring device for determining concentration of a first material in an environment in contact with the device, which first material reacts within said device in presence of a catalyst with a second material to form a third material; and which device comprises:

a membrane comprising a body, a surface in contact with said environment, and at least one discrete hydrophilic region in communication with said body, wherein said hydrophilic region is permeable to said first and second materials, and said body is otherwise permeable to said second material and essentially impermeable to said first material, wherein both said first and second materials diffuse into said device from said environment through said surface;

a catalyst within said hydrophilic region wherein reaction of said first and second materials occurs; at least one critical zone within said hydrophilic region containing said catalyst, said critical zone having an average equivalent radius and a length, wherein the average equivalent radius of said critical zone is less than said length of said critical zone, and wherein further the average vector direction of diffusion of said first material in said critical zone is substantially parallel to an average vector direction of diffusion of said first material in said hydrophilic region;

at least one sensor, having a surface communicating with at least one said hydrophilic region and sensitive to either said second material or said third material and producing a signal indicative of the concentration of said second or third material in said region; and a control responsive to said signal for comparing said signal to a reference to determine the concentration of said first material in said environment.

4. The measuring device of any of claims 1 through 3, wherein the environment is a biological fluid.

5. The measuring device of any of claims 1 through 3, wherein the environment is contacted by implantation of the sensor into an individual.

6. The measuring device of any of claims 1 through 3, wherein the bodily fluid is removed from an individual for contact with the sensor outside of the body.

7. The measuring device of any of claims 1 through 3, wherein the first material is glucose.

8. The measuring device of claim 7, wherein the catalyst is glucose oxidase.

9. The measuring device of any of claims 1 through 3, wherein the first material is lactate.

10. The measuring device of claim 9, wherein the catalyst is lactate oxidase.

11. The measuring device of any of claims 1 through 3, wherein the first material is cholesterol.

12. The measuring device of claim 11, wherein the catalyst is cholesterol oxidase.

13. The measuring device of any of claims 1 through 3, wherein the second material is oxygen.

14. The measuring device of any of claims 1 through 3, wherein the third material is hydrogen peroxide.

15. The measuring device of any of claims 1 through 3, wherein the membrane body is selected from the group of materials consisting of silicone-containing, ethylene-containing and propylene-containing polymers with and without fluorine, silicone rubbers, polyethylene, polypropylene, teflons and polyfluorinated hydrocarbons, poly-methyl-methacrylates, poly-carbonates, poly-hydroxyethyl-methacrylate, and co-polymers and combinations thereof.

16. The measuring device of any of claims 1 through 3, wherein the hydrophilic region is selected from the group of materials consisting of polyacrylamide gels, gluteraldehyde cross-linked proteins, vinyl pyrollidone, alginates, ethylene oxide, acrylamide, methylacrylic acids, poly-hydroxyethyl-methacrylate and its derivatives, and co-polymers and combinations thereof.

17. The measuring device of any of claims 1 through 3, wherein the hydrophilic region has essentially an identical surface area on the inner and outer faces of the membrane.

18. The measuring device of any of claims 1 through 3, wherein the hydrophilic region has a larger surface area on the inner face of the membrane as compared to the outer face of the membrane.

19. The measuring device of any of claims 1 through 3, wherein the membrane contains a plurality of hydrophilic regions.

20. The measuring device of claim 19, wherein the plurality of hydrophilic regions are a variety of sizes.

21. The measuring device of any of claims 1 through 3, wherein the critical zone is coincident with the hydrophilic region.

22. The measuring device of any of claims 1 through 3, wherein a single hydrophilic region corresponds to more than one sensor.

23. The measuring device of any of claims 1 through 3, wherein the base of the hydrophilic region is nearly identical in area to the area of its corresponding sensor.

24. The measuring device of any of claims 1 through 3, wherein the base of the hydrophilic region is larger in area than its corresponding sensor.

25. The measuring device of any of claims 1 through 3, wherein more than one hydrophilic region corresponds to a single sensor.

26. The measuring device of any of claims 1 through 3, wherein a single hydrophilic region corresponds to a plurality of sensors.

27. The measuring device of any of claims 1 through 3, wherein the environment is mammalian tissue.

* * * * *